United States Patent [19]

Alexander et al.

[11] 4,253,979

[45] Mar. 3, 1981

[54] LUBRICATING GREASE COMPOSITION CONTAINING PYRROLIDONE DERIVATIVE AS GREASE THICKENER

[75] Inventors: A. Gordon Alexander; Keith Coupland, both of Sarnia, Canada

[73] Assignee: Exxon Research & Engineering Co., Florham Park, N.J.

[21] Appl. No.: 9,742

[22] Filed: Feb. 5, 1979

[51] Int. Cl.³ .................. C10M 3/30; C10M 3/18; C10M 7/34; C10M 7/22
[52] U.S. Cl. .................. 252/33.6; 252/51.5 A
[58] Field of Search .................. 252/33.6, 51.5 A

[56] References Cited

U.S. PATENT DOCUMENTS

| | | | |
|---|---|---|---|
| 2,945,863 | 7/1960 | Berc et al. | 260/326.3 |
| 2,993,021 | 7/1961 | Bavley et al. | 260/30.2 |
| 3,035,907 | 5/1962 | Halter et al. | 44/71 |
| 3,224,968 | 12/1965 | Hinkamp | 252/33.6 |
| 3,224,975 | 12/1965 | Hinkamp | 252/51.5 A |
| 3,249,540 | 5/1966 | Gee et al. | 252/33.6 |
| 3,395,130 | 7/1968 | McDowell et al. | 260/78 |
| 3,758,407 | 9/1973 | Harting | 252/18 |
| 3,791,973 | 2/1974 | Gilani et al. | 252/41 |
| 3,929,651 | 12/1975 | Murray et al. | 252/41 |
| 4,127,493 | 11/1978 | Elliott et al. | 252/51.5 A |

*Primary Examiner*—Delbert E. Gantz
*Assistant Examiner*—Irving Vaughn
*Attorney, Agent, or Firm*—Eugene Zagarella

[57] ABSTRACT

A grease composition having excellent high temperature and multipurpose properties comprising a lubricating oil and an effective amount of a thickener which is a selected pyrrolidone compound.

19 Claims, No Drawings

LUBRICATING GREASE COMPOSITION CONTAINING PYRROLIDONE DERIVATIVE AS GREASE THICKENER

BACKGROUND OF THE INVENTION

This invention relates to a novel multipurpose lubricating grease composition having particularly desirable high temperature properties. More particularly, this invention involves a lubricating grease composition comprising a lubricating base oil and an effective amount of a selected pyrrolidone compound as the grease thickener.

A wide variety of thickening agents for greases have been developed over the years including the alkali salts of fatty acids, clays, polyureas, asbestos, carbon black, silica gels, aluminum complexes, polymers, phthalocyanine, indanthrene, etc. Despite the number and wide variety of such thickeners, over 90 percent of worldwide grease production uses alkali metal soaps as the thickening agent. The only nonsoap thickeners which have achieved commercial importance are the aluminum complexes, clays and polyureas and then only to a very limited extent.

The soap thickeners which have been mainly used are derived from the saponification of fats and oils by lithium and calcium hydroxides, although the sodium and barium soaps have been used in smaller amounts for special applications. The fats and oils are mostly mixtures of $C_{16}$ and $C_{18}$ fatty acid precursors with the preferred soap being lithium 12-hydroxystearate. This preferred lithium soap thickener constitutes over 50 percent of all greases and most all premium multipurpose greases. The lithium soap greases are described and exemplified in many patents including U.S. Pat. No. 3,758,407 issued to G. L. Harting on Sept. 11, 1973; U.S. Pat. No. 3,791,973 issued to S. Gilani et al on Feb. 12, 1974; and U.S. Pat. No. 3,929,651 issued to D. Murray et al on Dec. 30, 1975.

While a variety of thickeners have been developed, as noted above, they generally do not give equivalent performance to lithium 12-hydroxystearate, particularly in the critical areas of high temperature application, shear stability, water resistance and additive compatibility.

Although 12-hydroxystearic acid is the most desirable fatty acid grease thickening component, it does have some supply and economic problems associated with it and lithium, although readily available in many parts of the world, is expensive.

Accordingly, it is desired to develop a new grease thickener system that eliminates dependence on 12-hydroxystearic acid and reduces or eliminates lithium usage.

SUMMARY OF THE INVENTION

It has now been discovered that a multipurpose lubricating grease composition having improved properties, such as shear stability, reduced oil separability, additive compatibility, water resistance and excellent high temperature performance, is provided by a composition containing a selected pyrrolidone compound as a thickening agent.

DETAILED DESCRIPTION OF THE INVENTION

The present invention relates to a lubricating grease composition comprising a lubricating base oil and an effective amount of a selected pyrrolidone compound as thickening agent.

The pyrrolidone compound used in the lubricating grease composition of the invention is a derivative of 2-pyrrolidone-4-carboxylic acid and has the following general formula:

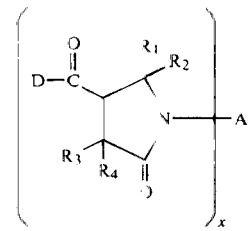

where x is 1 to 3, preferably 1 to 2, and more preferably 2; A is a hydrocarbyl group of 1 to 50 and preferably 1 to 25 carbon atoms; D is the residue or hydroxyl portion of the carboxylic acid group which can be optionally free or neutralized with a suitable metal, organo base or alcohol which provides one or two hydrocarbyl groups of 1 to 50, and preferably 1 to 30 carbon atoms, with the proviso that there is at least one long chain hydrocarbyl group of at least 12 carbon atoms present in either D or A; and $R_1$, $R_2$, $R_3$ and $R_4$ are each hydrogen or a hydrocarbyl group of 1 to 6 and preferably 1 to 4 carbon atoms.

More particularly, in the above formula, A is an alkyl, aryl, alkaryl or aralkyl group of 1 to 50, preferably 1 to 25 and more preferably 1 to 15 carbon atoms when x is 1, A is an alkylene, arylene, alkarylene or aralkylene of 1 to 50, preferably 1 to 25 and more preferably 12 to 22 carbon atoms when x is 2 and A is a trivalent hydrocarbyl radical of 1 to 50, and preferably 1 to 25 carbon atoms when x is 3. It is noted that the unsaturated counterparts of the A groups defined above may be used; however, the saturated groups are preferred. D is represented by an MO—,

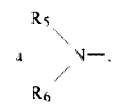

or an $R_7O$— group where M is a metal selected from Group I or Group II of the Periodic Table or aluminum and more particularly the alkali metals and the alkaline earth metals, i.e. lithium, sodium, calcium, barium, strontium and magnesium with lithium and sodium being preferred and more preferably lithium. $R_5$ and $R_6$ may each individually be a hydrocarbyl group and more particularly an alkyl, aryl, alkaryl or aralkyl group and the unsaturated counterparts thereof of 1 to 50, preferably 1 to 30 and more preferably 1 to 25 carbon atoms and one of $R_5$ or $R_6$ may be hydrogen. The groups as defined for $R_5$ and $R_6$ may include hetero oxygen or nitrogen atoms interspersed therein. Thus $R_5$ and $R_6$ groups may contain oxyalkylene groups, particularly oxyethylene and oxypropylene and also may contain nitrogen when a polyamine is used to neutralize the acid group. $R_7$ may be a hydrocarbyl group and more particularly an alkyl, aryl, alkaryl or aralkyl group and the unsaturated counterparts thereof of 1 to 50, preferably 1 to 30, and more preferably 1 to 25 carbon atoms and additionally, $R_7$ may be hydrogen. The saturated forms of $R_5$, $R_6$ and $R_7$ are particularly preferred. $R_1$, $R_2$, $R_3$ and $R_4$ in the above structure will particularly be hydrogen or alkyl of 1 to 6 and preferably 1 to 4 carbon atoms. It is more preferable that such R groups are hydrogen.

In the above-described pyrrolidone compound, A may include hetero oxygen, sulfur, and nitrogen groups and the term "alkyl" may include cyclic structures. It is further understood that branch-chained structures and other isomers thereof are contemplated by the described pyrrolidone structure. The functional D groups may be the same or different when more than one is present. In accordance with the previous description there may be different combinations of the above A and D groups with the proviso that at least one substantially oil-soluble group, i.e. a long chain hydrocarbon group of at least 12 carbon atoms, is present.

The basic pyrrolidone structure used in preparing the grease thickeners of this invention is 1-substituted-2-pyrrolidone-4-carboxylic acid which is obtained by reacting a suitable primary amine with an α-alkylidene substituted carboxylic acid or ester which preferably is itaconic acid. This is a well-known reaction which is used to obtain intermediates for the plastic industry as disclosed in U.S. Pat. Nos. 2,993,021, issued to A. Bavley et al on July 18, 1961, and 3,395,130, issued to R. McDowell et al on July 30, 1968.

The 1-substituted-2-pyrrolidone-4-carboxylic acid, as described above, is then reacted with suitable amines to form the amide derivative, with an alcohol to form the ester derivative, or with suitable inorganic compounds, e.g. hydroxides, carbonates and alkoxides to yield the metal salt. As indicated above, when there is more than one carboxyl group on the starting pyrrolidone compound, different functional groups, i.e. D as shown on the above-designated formula, may be added to each. This is accomplished by using the appropriate molar proportions of the respective starting materials needed to provide the desired functional groups. One example of this is when a bispyrrolidone made from a diamine and preferably an aromatic diamine is condensed with an amine, preferably a long chain fatty amine to form an amide derivative with one carboxyl group and the other carboxyl group is neutralized with a metal salt.

The amines useful in preparing the pyrrolidone amide derivatives of this invention may be a primary or secondary amine and may be a mono-, di- or polyamine. Illustrative examples of such amines include the following: methylamine, ethylamine, diethylamine, ethylene diamine, n-propylamine, isopropylamine, amylamine, cyclohexylamine, octylamine, dioctylamine, decylamine, dodecylamine, hexadecylamine, octadecylamine, dioctadecylamine, coco amine, dicoco amine, N-coco-trimethylenediamine, tallow amine, di-cosylamine, eicosyl-docosylamine, di(eicosyl-docosyl) amine, N-octadecenyltrimethylene diamine, aniline, toluidene, xylidene, N-methylaniline, benzylamine, diphenylamine, amines derived from rapeseed oil, phenethylamine, mixtures of amines such as Primene 81-R (principally t-$C_{12}H_{25}NH_2$ to t-$C_{14}H_{29}NH_2$) and Primene JM-T (principally t-$C_{18}H_{37}NH_2$ to t-$C_{22}H_{45}NH_2$). Mixtures of these and other amines may also be employed. Further examples of amines which may be used are disclosed in Kirk-Othmer *Encyclopedia of Chemical Technology*, Second Edition, Vol. 2, 1963, pp. 99–138 and 411–426.

Alcohols and other hydroxy compounds useful in preparing the pyrrolidone ester derivative include: ethyl alcohol, butyl alcohol, n-decyl alcohol, cetyl alcohol, stearyl alcohol, eicosonyl alcohol, hentriacontanol, phenol, benzyl alcohol and phenylethyl alcohol. Other useful alcohols are disclosed in Kirk-Othmer *Encyclopedia of Chemical Technology*, Second Edition, Vol. 1, 1963, pp 531–568.

The metal compounds useful in preparing the salt derivative of pyrrolidone include the hydroxides, carbonates and alkoxides of the respective selected metals.

The amines which may be used in preparing the basic or precursor pyrrolidone compound will of course depend on the desired A group in the final pyrrolidone compound. Such amines include phenylamine (aniline), phenylene diamine, phenylene di(methylamine), naphthylene diamine, 4,4'-bisphenylene diamine, 4,4'-thiobisphenylene diamine, 4,4'-oxybisphenylene diamine, 4,4'-methylenebisphenylene diamine, 4,4'-isopropylidenebisphenylene diamine, octadecylamine, octadecyldiamine, amines of polyisobutylene (up to about 50 carbons) and other amines as described in the earlier description.

The total pyrrolidone thickener content of the grease composition of this invention will range from about 1 to about 60 wt.% and preferably about 2 to about 50 wt.% and more preferably about 5 to about 30 wt.% based on the total composition.

The lubricating base oil that is used in preparing the grease compositions of this invention can be any of the conventionally used mineral oils, synthetic hydrocarbon oils or synthetic ester oils. In general, these lubricating oils will have a viscosity in the range of about 35 to 200 SUS at 210° F. Mineral lubricating oil base stocks used in preparing the greases can be any conventionally refined base stocks derived from paraffinic, naphthenic and mixed base crudes. Synthetic lubricating oils that can be used include esters of dibasic acids, such as di-2-ethylhexyl sebacate, esters of poly glycols such as trimethylol propane tricaprylate, pentaerythritol tetraoctanoate, dipentaerythritol tricaprylate tripelargonate, esters of glycols such as a $C_{13}$ oxo acid diester of tetraethylene glycol, or complex esters such as one formed from 1 mole of sebacic acid and 2 moles of tetraethylene glycol and 2 moles of 2-ethylhexanoic acid. Other synthetic oils that can be used include synthetic hydrocarbons such as alkyl benzenes, e.g., alkylate bottoms from the alkylation of benzene with tetrapropylene, or the copolymers of ethylene and propylene; silicone oils, e.g., ethyl phenyl polysiloxanes, methyl polysiloxanes, etc., polyglycol oils, e.g., those obtained by condensing butyl alcohol with propylene oxide; carbonate esters, e.g., the product of reacting $C_8$ oxo alcohol with ethyl carbonate to form a half ester followed by reaction of the latter with tetraethylene glycol, etc. Other suitable synthetic oils include the polyphenyl ethers, e.g., those having from about 3 to 7 ether linkages and about 4 to 8 phenyl groups. (See U.S. Pat. No. 3,424,678, col. 3.). Preferably the lubricating base oil will comprise the major amount of the grease composition.

The grease composition of this invention can be prepared in accordance with any of the techniques known in the prior art and such composition may include other additive components, e.g., dyes, antioxidants, anticorrosion agents, lubricity additives, etc., which are conventionally found in grease compositions.

The following examples are set forth to illustrate the invention and should not be construed as limitations thereof.

EXAMPLE 1

A grease composition was prepared by first mixing 300 grams of solvent 600 N oil with 0.25 mole of 4,4'-methylene dianiline (49.5 g; 4.6 wt.%) and 0.5 mole of itaconic acid (65.0 g; 6.04 wt.%) at room temperature to form a slurry. The temperature was raised to 107° C. (225° F.) and the chemicals reacted to form a sticky mass under the oil. The temperature was raised to 121° C. (250° L F.) with stirring, the water of reaction was driven off and the mass became a granular solid which when the stirring was stopped, settled out. Total reaction time was about 20 minutes and the slurry was stirred for one hour at 121° L C. (250° F.) to ensure complete reaction.

Octadecylamine (0.25 mole-67.4 g, 6.27 wt.%) was added at 121° C. (250° F.) and the mass began to thicken to a grease-like consistency within 10 to 15 minutes. The temperature was raised to 163° C. (325° F.) and the mass quickly softened to a fairly smooth thick cream. The temperature was then slowly raised to 204° C. (400° F.) during which water of reaction was driven off to form a hard soap. An additional 152 g of the oil was added as the mass was cooled to approximately 93° C. (200° F.).

One-quarter (0.25) mole of $LiOH.H_2O$ (0.98 wt.%) in 100 ml of water was added and the mass slowly raised to 163° C. (325° F.) for one-half hour to complete dehydration. The temperature was then raised to 218° C. (425° F.) for a short time to complete cookout during which the mass became quite hard. The mass was cooled and an additional 331 g of oil added to yield a light brown grease. The product was milled and an additional 100 g of oil was added to yield the final product. The total amount of oil used was 883.0 grams (82.11 wt.%). The thickener may be represented by the formula:

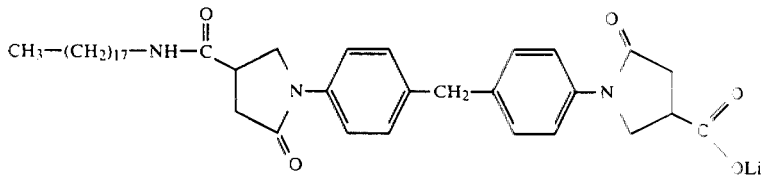

The grease produced was evaluated and found to have the following properties:

| | |
|---|---|
| Color (visual) | light brown |
| Consistency (visual) | smooth and buttery |
| Penetration, mm/10, 25° C. (77° F.), (ASTM D217) | |
| unworked | 282 |
| 60 strokes | 270 |
| 100,000 strokes | 299 |
| Dropping point (ASTM 566) | >316° C. (600° F.) |
| Rust Test (ASTM D1743) | 1,1,1 (Pass) |
| Water Resistance (100g grease/100g water/60 minutes/room temp./ASTM Roller) | |
| water absorption, g | 92 |
| metal adhesion | excellent |
| change in penetration | −14mm/10 |
| Wheel bearing test, 163° C. (325° F.), (ASTM D1263) | |
| leakage | 1.6g |
| slump | nil |
| Wheel bearing test, 163° C. (325° F.) (ASTM D1263) (containing commercial grease additive package with antiwear, antirust and load-carrying additives) | |
| leakage | 1.1g |
| slump | nil |
| Spindle bearing life, 177° C. (350° F.) (ASTM 3336) (containing commercial antifriction bearing grease additive package with antioxidants and rust inhibitors) | |
| running time | 271 hours (ave. 3 runs) |

EXAMPLE 2

A grease product similar to Example 1 was prepared in the same manner using a total of 796 g of solvent 600 N oil (77.86 wt.%)

- 0.25 mol of 4,4'-methylene dianiline (49.5 g, 4.84 wt.%),
- 0.5 mole of itaconic acid (65.0 g, 6.36 wt.%),
- 0.25 mole octadecylamine (67.4 g, 6.59 wt.%), and
- 0.25 mole $LiOH.H_2O$ (10.5 g, 1.03 wt.%).

Azelaic acid (0.125 mole, 23.5 g, 2.3 wt.%) was added to the above grease product with an additional equivalent amount of $LiOH.H_2O$ to that noted above added in water to effect neutralization. The temperature was raised to allow dehydration and the mass cooked out at about 232° C. (450° F.) to improve the grease structure. As the mass cooled, additional oil (part of the total amount stated above) was added and the grease milled at room temperature to yield a fairly smooth light brown product which was evaluated and found to have the following properties:

| | |
|---|---|
| Penetration, mm/10, 25° C. (77° F.) | |
| unworked | 261 |
| 60 strokes | 263 |
| 100,000 strokes | 306 |
| Dropping point | >316° C. (600° F.) |
| Water resistance | |
| water absorbed | 81g |
| adhesion | excellent |
| Δ penetration | −3mm/10 |

EXAMPLE 3

A grease product similar to Example 1 was prepared using 418.1 g (69.69 wt.%) of solvent 600 N oil, 49.5 g (8.25 wt.%, 0.25 mole) of 4,4'-methylenedianiline, 65.0 g (10.83 wt.%, 0.5 mole) of itaconic acid and 67.4 g (11.23 wt.%, 0.25 mole) of octadecylamine.

The ingredients were reacted as described in Example 1 and the resultant product was a light brown grease with a free carboxylic acid function rather than the salt derivative as in Example 1 and having the following properties:

| | |
|---|---|
| Penetration, mm/10, 25° C. (77° F.) | |
| unworked | 276 |
| 60 strokes | 283 |
| Dropping Point | 278° C. (533° F.) |

EXAMPLE 4

A grease product similar to Example 1 was prepared using 559.0 g (75.03 wt.%) of solvent 600 N oil, 106.5 g (14.30 wt.%, 0.25 mole) of the bispyrrolidone reaction product derived from the reaction of 49.5 g (0.25 mole) of 4,4'-methylenedianiline with 65.0 g (0.50 mole) of itaconic acid and 69.5 g. (9.33 wt.%, 0.25 mole) of octadecylamine (commercially available as Armeen 18D from Armak Chemical Ltd.)

The ingredients were reacted in a similar manner to Example 1. Complete neutralization was accomplished by cooling the mass to 149° C. (300° F.) and 10.0 g (1.34 wt.%, 0.25 mole) of NaOH in 50 ml of water was slowly added. The temperature was raised to 232° C. (450° F.) for 15 minutes to complete the reaction and to insure proper dispersion. The product had the following properties:

| Penetration, mm/10, 25° C. (77° F.) | |
|---|---|
| unworked | 268 |
| 60 strokes | 263 |
| 100,000 strokes | 306 |
| Dropping point | >316° C. (>600° F.) |
| Rust test | 1,1,1 (Pass) |
| Water resistance | |
| water absorbed | 35g |
| metal adhesion | fairly good |
| $\Delta$ penetration | −9 mm/10 |
| Wheel bearing test (163° C.; 325° F.) | |
| leakage | 0.3g |
| slump | nil |

EXAMPLE 5

A grease product similar to those previously described in the other examples was prepared using 611.0 g (71.34 wt.%) of solvent 600 N oil, 106.5 g (12.43 wt.%, 0.25 mole) of the bispyrrolidone reaction product derived from the reaction of 1 mole of 4,4'-methylenedianiline with 2 moles of itaconic acid and 139.0 g (16.23 wt.%, 0.5 mole) of octadecylamine (Armeen 18D).

The octadecylamine was dissolved in about one-half of the oil (300 g) at 135° C. (275° F.) with stirring. The bispyrrolidone reaction product was slowly added and a paste formed. The temperature was raised and at 163° C. (325° F.) a slurry formed. The temperature was again raised to 177° C. (350° F.) and the mass thickened as water was driven off over one-half hour. The reaction and dispersion was completed at 204° C. (400° F.) to give a smooth grease. The mass was cooled to room temperature with oiling to give a product with the following properties:

| Penetration, mm/10, 25° C. (77° F.) | |
|---|---|
| unworked | 281 |
| 60 strokes | 291 |
| 100,00 strokes | 286 |
| Dropping point | 243° C. (470° F.) |
| Water resistance | good metal adhesion |

EXAMPLE 6

A grease product similar to those previously described in the other examples was prepared using 922.0 g (81.09 wt.%) of solvent 600 N oil, 106.0 g (9.32 wt.%, 0.25 mole) of the bispyrrolidone reaction product derived from the reaction of 1 mole of 4,4'-methylenedianiline with 2 moles of itaconic acid, 78.75 g (6.93 wt.%, 0.25 mole) of a commercial grade amine derived from hydrogenated high erucic acid rapeseed oil (Armeen HR) and 30.25 g (2.66 wt.%), 0.25 mole) of phenethylamine.

The Armeen HR amine was dissolved in 300 g of oil at 121° C. (250° F.) with stirring. The bispyrrolidone reaction product was slowly added over 1.5 hours as the temperature was raised to 177° C. (350° F.). The mass was cooled to 93° C. (200° F.) with oiling (300 g) to yield a product with approximately an NLCI #2 grade consistency. The phenethylamine was slowly dripped in which caused hardening of the mass. Additional oil was added while stirring. The temperature was slowly raised to 204° C. (400° F.) over a two-hour period before cooling to room temperature with final oiling to yield a smooth buttery grease with the following properties:

| Penetration, mm/10, 25°C. (77° F.) | |
|---|---|
| unworked | 282 |
| 60 strokes | 282 |
| 100,00 strokes | 325 |
| Dropping point | 261° C. (501° F.) |
| Water resistance | good metal adhesion |

What is claimed is:

1. A lubricating grease composition comprising a lubricating oil and an effective amount of a pyrrolidone compound as a thickener, said pyrrolidone compound having the formula:

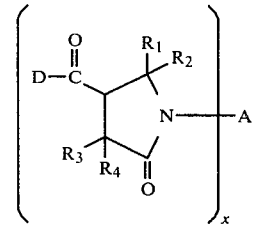

where x is 1 to 3, A is a hydrocarbyl group of 1 to 50 carbon atoms, D is an MO—

or R$_7$O— group where M is a metal selected from Group I or II of the Periodic Table or aluminum, R$_5$ and R$_6$ are each a hydrocarbyl group of 1 to 50 carbon atoms and one may be hydrogen, R$_7$ is a hydrocarbyl group of 1 to 50 carbon atoms or hydrogen with the proviso that there is at least one long chain hydrocarbon group of at least 12 carbon atoms present in either D or A, and R$_1$, R$_2$, R$_3$ and R$_4$ are hydrogen or an alkyl group of 1 to 6 carbon atoms.

2. The composition of claim 1 wherein x is 1 or 2, A is an alkyl, aryl, alkaryl or aralkyl and the unsaturated counterparts thereof of 1 to 25 carbon atoms when x is 1, and A is an alkylene, arylene, alkarylene or aralkylene and the unsaturated counterparts thereof of 1 to 25 carbon atoms when x is 2 and wherein said thickener is used at a concentration of about 1 to about 60 weight percent based on the total weight of the composition.

3. The composition of claim 2 wherein M is a metal selected from the group consisting of lithium, sodium, calcium, barium, strontium, magnesium and aluminum.

4. The composition of claim 3 wherein $R_5$ and $R_6$ are each an alkyl, aryl, alkaryl, or aralkyl group and the unsaturated counterparts thereof of 1 to 30 carbon atoms and one of $R_5$ and $R_6$ may be hydrogen.

5. The composition of claim 4 wherein said thickener is used in a concentration of about 2 to about 50 weight percent based on the total weight of the composition and $R_7$ is an alkyl, aryl, alkaryl or aralkyl group and the unsaturated counterparts thereof 1 to 30 carbon atoms or hydrogen.

6. The composition of claim 5 wherein M is lithium or sodium.

7. The composition of claim 6 wherein said thickener is used in a concentration of about 5 to about 30 wt.% based on the total weight of the composition.

8. The composition of claim 7 wherein $R_5$ and $R_6$ each contain 1 to 25 carbon atoms and one of $R_5$ and $R_6$ may be hydrogen and $R_7$ contains 1 to 25 carbon atoms or hydrogen.

9. The composition of claim 6 wherein x is 2.

10. The composition of claim 9 wherein one D is an MO— group and one D is an

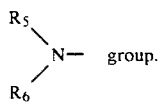

group.

11. The composition of claim 10 wherein M is lithium and $R_1$, $R_2$, $R_3$ and $R_4$ are hydrogen.

12. The composition of claim 11 wherein D is derived from octadecylamine, tallow amine or an amine of rapeseed oil.

13. The composition of claim 12 wherein A is a 4,4'-methylenebisphenylene radical.

14. The composition of claim 9 wherein one D is derived from octadecylamine and the other D is $R_7O$— where $R_7$ is hydrogen, A is 4,4'-methylenebisphenylene, and $R_1$, $R_2$, $R_3$ and $R_4$ are hydrogen.

15. The composition of claim 10 wherein M is sodium and $R_1$, $R_2$, $R_3$ and $R_4$ are hydrogen.

16. The composition of claim 15 wherein D is derived from octadecylamine and A is a 4,4'-methylenebisphenylene radical.

17. The composition of claim 10 wherein both D groups are derived from octadecylamine and A is a 4,4'-methylenebisphenylene radical.

18. The composition of claim 10 where one D group is derived from phenethylamine, the other D group is derived from an amine formed from rapeseed oil.

19. The composition of claim 7 wherein x is 2 and A is derived from amines selected from the group consisting of phenylene diamine, phenylene di(methylamine), naphthylene diamine, 4,4'-bisphenylene diamine, 4,4'-thiobisphenylene diamine, 4,4'-oxybisphenylene diamine, 4,4'-methylenebisphenylene diamine, 4,4'-isopropylidene diamine and octadecyldiamine.

* * * * *